(12) United States Patent
Tatarek

(10) Patent No.: US 8,448,643 B2
(45) Date of Patent: May 28, 2013

(54) MEDICAL BREATHING APPARATUS

(75) Inventor: Andrew Richard Thomas Tatarek, Hampshire (GB)

(73) Assignee: Concept 2 Manufacture Design Ltd, Aldershot, Hampshire (GB)

(*) Notice: Subject to any disclaimer, the term of this patent is extended or adjusted under 35 U.S.C. 154(b) by 917 days.

(21) Appl. No.: 11/720,816

(22) PCT Filed: Dec. 2, 2005

(86) PCT No.: PCT/GB2005/050230
§ 371 (c)(1),
(2), (4) Date: Jul. 20, 2009

(87) PCT Pub. No.: WO2006/059161
PCT Pub. Date: Jun. 8, 2006

(65) Prior Publication Data
US 2009/0293878 A1   Dec. 3, 2009

(30) Foreign Application Priority Data
Dec. 4, 2004   (GB) .................................. 0426676.3

(51) Int. Cl.
*A62B 9/00*   (2006.01)
(52) U.S. Cl.
USPC ............. 128/204.26; 128/200.24; 128/204.16
(58) Field of Classification Search
USPC ............. 128/200.24, 204.18, 204.16, 205.24, 128/204.26
See application file for complete search history.

(56) References Cited

U.S. PATENT DOCUMENTS

| | | | |
|---|---|---|---|
| 3,050,054 A * | 8/1962 | Jones | 128/204.29 |
| 3,526,241 A * | 9/1970 | Veit | 137/81.1 |
| 3,616,813 A | 11/1971 | Nelson | |
| 5,301,667 A | 4/1994 | McGrail et al. | |
| 5,871,011 A | 2/1999 | Howell et al. | |
| 2002/0195108 A1 | 12/2002 | Mittelstadt et al. | |
| 2004/0094157 A1 | 5/2004 | Dantanarayana et al. | |
| 2004/0200474 A1 | 10/2004 | Lurie | |

FOREIGN PATENT DOCUMENTS

| | | |
|---|---|---|
| EP | 0 249 322 A1 | 12/1987 |
| EP | 0 582 419 A1 | 2/1994 |
| EP | 0 610 054 A1 | 8/1994 |
| EP | 0 911 050 A2 | 4/1999 |
| FR | 2 276 064 | 1/1976 |
| GB | 1034759 | 7/1966 |
| WO | WO-02/094360 | 11/2002 |

OTHER PUBLICATIONS

Intersurgical Product Catalogue extracts; Edition 4; Intersurgical Complete Respiratory Systems; Mar. 2004.

* cited by examiner

*Primary Examiner* — Glenn Richman
(74) *Attorney, Agent, or Firm* — Alston & Bird LLP

(57) ABSTRACT

A medical breathing apparatus incorporating a regulator for supplying breathing gas to a patient from an air hose (11). The regulator supplies breathing gas on demand to the patient via a mouthpiece or similar attached to an output connector (55). The connector forms part of a removable output unit (4) incorporating a filter (53) and an exhale flap valve (57/58) on the patient side of the filter. When the patient exhales, exhaled gas entering the connector (55) exits to atmosphere via the exhale valve without passing through the filter into the interior of the regulator, thus reducing cross-contamination between patients. Also described is an improved valve seat (16)/valve member (18) assembly in which multiple spaced pivot points (22, 23) are defined to cause the mechanical advantage for operating the valve member to reduce as the valve opens, thus reducing the force needed to operate the valve at lower flow rates.

21 Claims, 5 Drawing Sheets

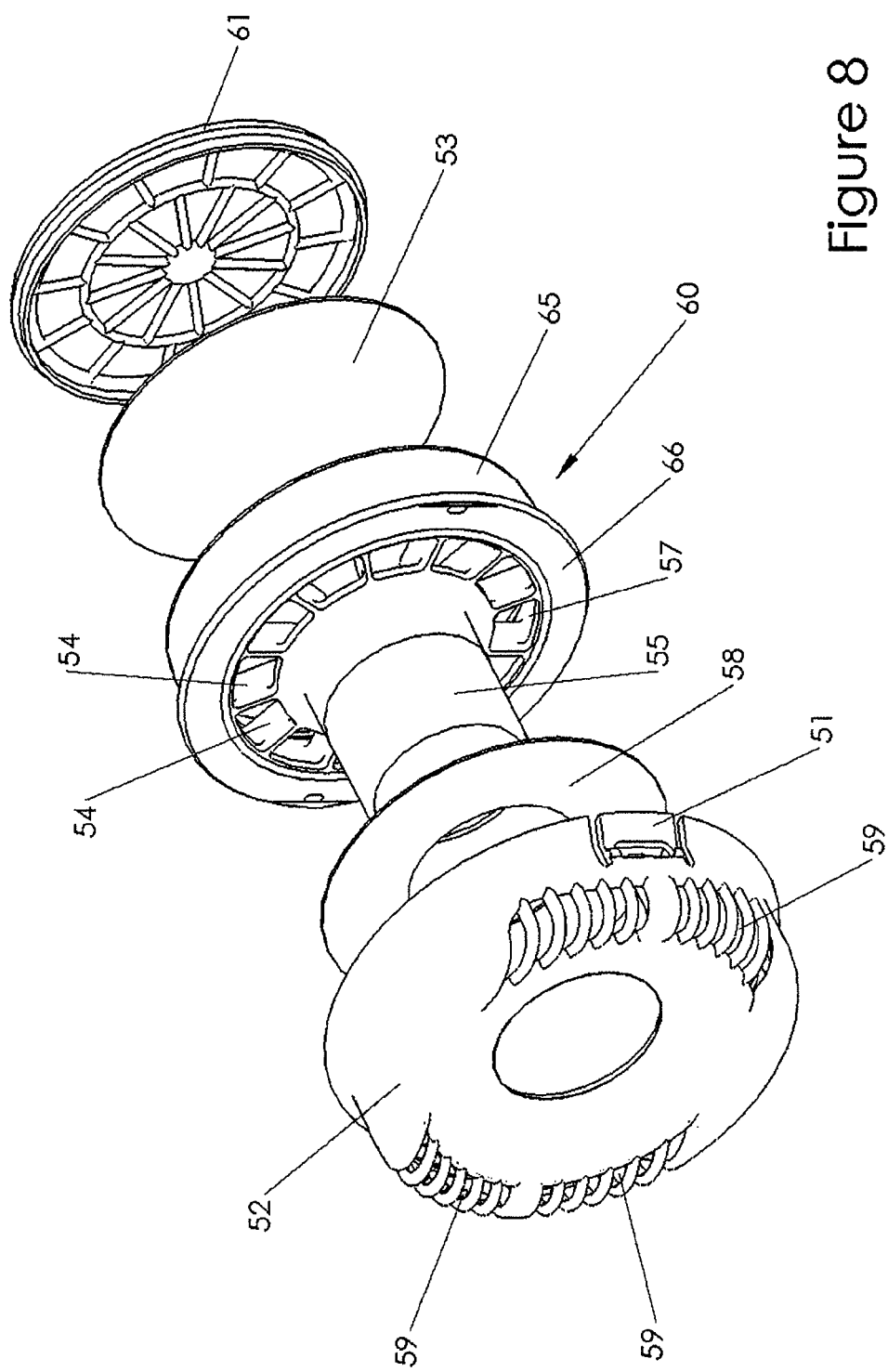

MEDICAL BREATHING APPARATUS

This invention relates to medical breathing apparatus of the type incorporating a regulator for supplying breathing gas to a patient.

Breathing apparatus incorporating regulators are used in a variety of fields, for example for delivery of 50/50 $N_2O/O_2$ mixtures (used in pain relief in childbirth, wound dressing, limb resetting and other applications) or oxygen for 100% therapy (used in resuscitation, treatment for smoke inhalation and many other uses). They can also be used with other gases.

The regulator is connected to a supply of medium pressure gas, for example of 3-6 bar, such as a cylinder or a gas pipeline. The outlet of the regulator is connected to a user or patient's mouth via a mask or a mouthpiece. As the user draws gas from the apparatus, the regulator supplies gas flow matching the demand, maintaining a roughly constant pressure that is in keeping with what can readily be drawn by a patient (in the region of 250 Pa-1000 Pa below atmospheric) at the outlet. This type of regulator is sometimes called a "demand valve". Typical demand valves of this type are described in EP-A-0249322, EP-A-0582419 and EP-A-610054.

Existing products have a number of drawbacks with regard to prevention of cross-infection. There is a risk of infectious particles from the breath of a patient being transferred to the regulator, and then from the regulator to the next patient. To prevent this, typically the unit is taken apart to be cleaned between each patient, a process which can take time, is difficult to do properly, and may easily get missed in a busy hospital environment. Alternatively the regulator may be used with an in-line single use filter on its outlet. This type of filter provides a barrier between the patient and the regulator. The patient breathes in through the filter, and then exhales through it, with the intention that the filter prevents pathogens contaminating the regulator.

These medical in-line filters are typically designed for respiratory circuit use, where the patient is sedentary or unconscious, and, as such, are designed and tested for peak flows of 60 L/m. Often, the filters are not tested at the 200 L/m flows demanded by patients, so bacteria, viruses and other pathogens may get through at 200 L/m even if they do not pass at 60 L/m. Filter efficiency decreases disproportionately with flow, so a filter that just passes requirements at 60 L/m will allow many times more than three times the amount of contaminants at 200 L/m. A suitable filter medium for a peak flow of 200 or more L/m would require over three times the area to have a reasonably low resistance, so would dwarf the typical regulator, and be so large as to be impractical.

In-line filters have three major disadvantages with regard to use with a medical regulator:

1) The large bulk and length of the filter in addition to the size of the regulator makes for a large unwieldy package for the patient to hold. There are two joints, one at each end of the filter, with potential for coming apart or leaking.

2) This size and bulk adds to the discomfort of holding, exacerbating the discomfort of the patient.

3) Since the filters are designed for low flows, their resistance at high flows needed, for example by mothers in childbirth, are very high. This high filter resistance makes for hard work in breathing, and this is on top of the regulator resistance.

A custom disposable filter (where the filter is part of the outlet) could reduce some of these problems, but would not solve the fundamental problem of the area of filtration medium required, so the regulator with a filter in the outlet would either be very large or would still have the high resistance to flow and the resultant discomfort to patients.

The present invention seeks to provide medical breathing apparatus incorporating a regulator of high robustness, which achieves better cross contamination protection whilst at the same time overcoming the limitations of filter size and resistance.

In a first aspect of the invention the regulator is fitted with a removable outlet unit, with a contamination barrier arranged such that clean gas from the regulator passes through the contamination barrier, and contaminated exhaled gas bypasses the contamination barrier and is exhaled to ambient atmosphere. The outlet unit may be constructed such that all the parts of it that come into contact with the contaminated gas are disposable for single patient use. Further the construction may be such that none of the exhaled gas comes into contact with any part of the regulator.

Thus, according to the first aspect of the invention there is provided medical breathing apparatus incorporating a regulator for regulating an input supply of breathing gas and passing the gas on demand to an outlet for application to a patient, said apparatus being characterised in that said outlet comprises a removable outlet unit comprising a contamination barrier for resisting the passage of exhaled air to said regulator, and an exhale valve on the downstream side of the contamination barrier with respect to the supply of breathing gas.

Thus breathing gas passes from the gas source, which may for example be a cylinder or gas pipeline, through the regulator which supplies breathing gas on demand to a patient, at a level suitable for application to a patient, and finally through the contamination barrier to the patient. The regulator is opened to supply gas when the patient inhales, this causing a negative pressure which is sensed by the regulator. When the patient exhales, gas passes back into the outlet and, in prior art devices, passes through a filter to an exhale valve on the upstream side of the filter with respect to the direction of supply of breathable gas. The increased pressure resulting from exhalation causes the regulator to close, thus shutting off the supply of breathing gas, and also opens the exhale valve to enable the exhaled air to be expelled.

In the apparatus of the present invention, the exhale valve is situated in a position downstream of the filter with respect to the supply of breathable gas—i.e. on the patient side of the filter. This means that the contamination barrier does not have to pass exhaled air, and thus allows it to have the sole function, during exhalation, of preventing, as far as possible, the contaminated exhaled air from passing back into those parts of the apparatus—principally the regulator—which are not removable and are thus not potentially disposable. In other words, all parts of the apparatus which are contaminated by the patients exhaled breath, including the contamination barrier itself, are disposable. The contamination barrier may take the form of a one-way valve, for example a flap valve, which allows passage of gas from the supply to the patient during inhalation, but blocks it during exhalation. The main problem with such a valve is that it requires a small positive pressure on its downstream (patient) side to close and this inevitably means that, before this pressure is reached during exhalation, a tiny amount of contaminated exhaled gas may leak through the valve.

Preferably the contamination barrier takes the form of a filter which has the potential, aside from small circulatory air currents caused, for example by Brownian motion, to provide a substantially complete barrier against contaminated exhaled gas. To achieve this, in a preferred embodiment of the invention, the regulator valve is designed to close prior to the commencement of exhalation so that exhaled gas cannot pass through the filter into the regulator at all, and instead takes the preferential route through the exhale valve. The regulator operates by sensing the negative inhale pressure and can be designed to open only when a predetermined minimum negative pressure—determined by the physical characteristics of the components—is exceeded. As the patient's demand increases, so the negative pressure increases, and the valve opens further and further to supply an increasing flow rate to the patient. As the inhalation phase draws to a close, the opposite happens—the valve gradually closes until, at a certain negative pressure below that of atmospheric, the valve closes. Thus, by the time the patient has ceased inhaling, the valve has closed, thus effectively sealing the regulator from reverse flow from the patient prior to exhalation.

Preferably, the exhale valve is of the simple flap type. With the opening of the exhale valve, exhaled gas bypasses the contamination barrier, and flows straight out through the exhale valve. When the patient subsequently starts to inhale, the pressure at the outlet falls again, thus closing the exhale valve, and allowing the negative pressure to be felt through the filter in order to re-open the regulator.

In the preferred embodiment of the invention, the regulator is fitted in a body which incorporates an inlet for connection to the supply of breathable gas. The outlet unit is removably attached to this body, for example by way of an outlet flange on the body, and means are preferably provided for maintaining the outlet unit in place. To this end, releasable fastening clips may be used to join the outlet unit to the regulator body. Alternatively a readily-releasable bayonet or screw-type connection, or a push-in taper may be used to connect the two.

The outlet unit, including the contamination barrier, can thus be regarded as essentially disposable and the intention is that it be replaced for a new unit between each patient. This greatly reduces the risk of cross-contamination between patients.

Regulators of the type with which the present invention is concerned typically comprise some form of pressure sensor such as a diaphragm which is mechanically connected to a valve member which is operable to open and close a valve in accordance with the sensed pressure. A problem arises because the valve must securely close the supply when gas is not needed and, with typical cylinder/supply line pressures in the range 3-6 bar, considerable force is necessary to open and close the valve as needed. To overcome this, most regulators incorporate a significant mechanical advantage, so that the relatively small changes in pressure which are used to sense inhalation and exhalation can be utilised to reliably and safely operate the valve.

It will be seen that the amount of mechanical advantage will control the ease with which inhalation pressure will cause the apparatus to operate. The official requirements for medical regulator inhalation resistance, as reflected for example in British standard BS4272, is for low resistance at low gas flows, for example to allow easy inhalation for use with children; however, slightly higher inhalation pressure is permissible at higher flows.

To cater for this, a second aspect of the present invention provides for the mechanical advantage to be reduced at greater flow rates. Thus, in accordance with the second aspect of the invention there is provided medical breathing apparatus incorporating a regulator for regulating an input supply of breathing gas and passing the gas on demand to an outlet for application to a patient, said apparatus being characterised in that said regulator includes a valve comprising a valve seat and associated valve member which is tiltable with respect to said valve seat to open and close the valve, and wherein there are provided two or more spaced pivot points between the valve member and valve seat, about which pivot points the valve member and valve seat progressively pivot as the valve moves from the closed position to the open position and vice versa.

As will be explained, by appropriate positioning of the pivot points, it can be arranged that the pressure needed to operate the valve can be relatively low at zero and low flow rates, but can increase by one or more steps (depending on the number of pivot points) a the valve opens further, and the flow rate thus increases.

In order that the invention may be better understood, an embodiment thereof will now be described by way of example only and with reference to the accompanying drawings in which:

FIGS. 1 and 2 show a side sectional elevation of one embodiment of a medical breathing apparatus according to the invention, in which FIG. 1 shows the regulator valve closed, and FIG. 2 shows the regulator valve open;

FIG. 8 is an exploded perspective view of the disposable outlet unit.

Figure 1:
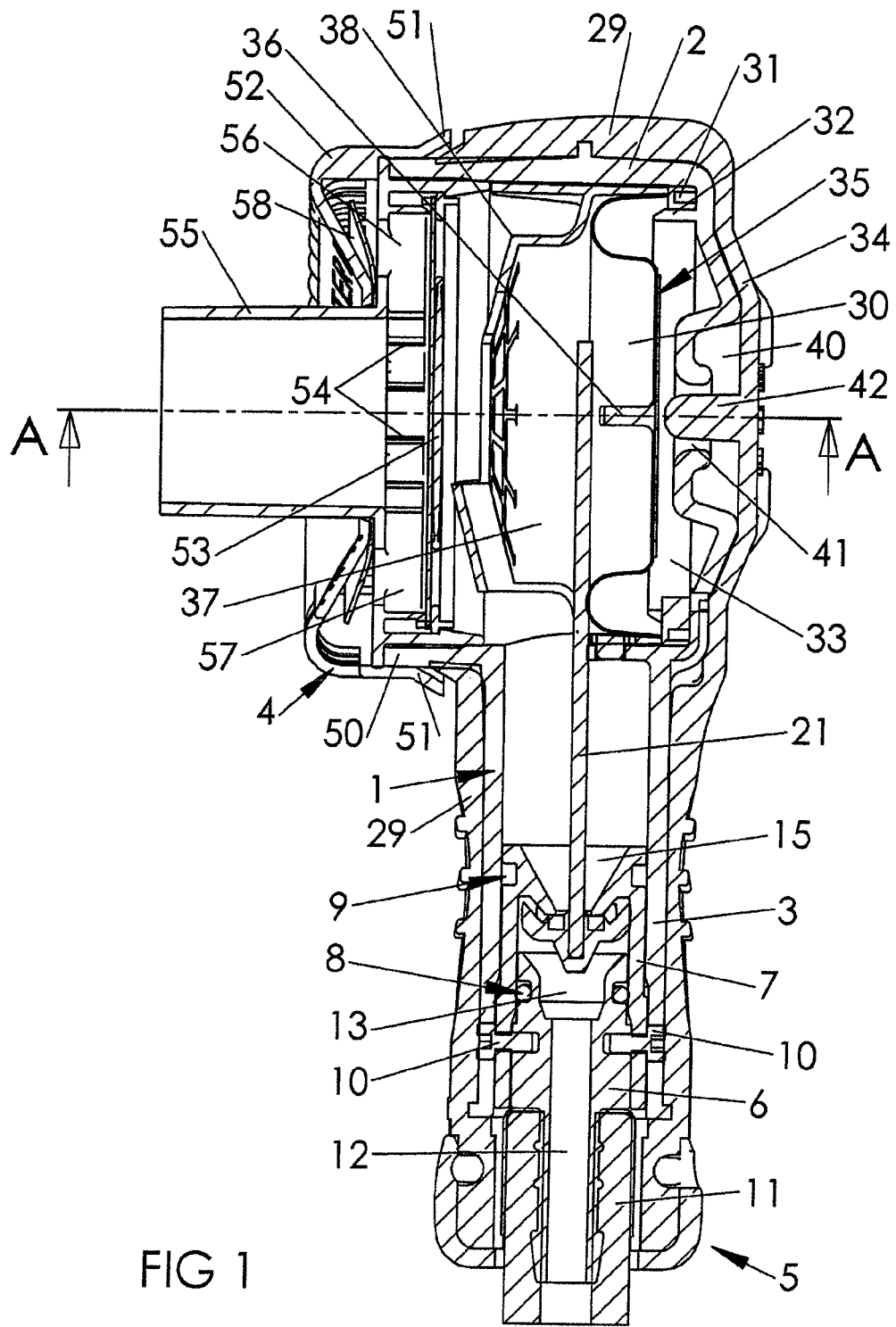

The breathing apparatus comprises a body 1 of semi-rigid plastics material around which is formed a single-piece cover layer 29 of softer material, typically an elastomeric material such as silicone rubber, to make the apparatus more comfortable to use, easy to clean and to provide protection against knocks. The body 1 is generally divided into two hollow cylindrical portions: an upper portion 2 having a horizontal axis with respect to FIG. 1, and a lower portion 3 which has a vertical axis with respect to FIG. 1. The upper portion 2 is equipped with an outlet unit 4 through which a patient receives breathing gas via a contamination barrier in the form of a filter, while the lower portion is equipped with an inlet section 5 through which gas at medium pressure, typically 3 to 6 bar, is supplied from a cylinder or supply line (not shown). The lower portion also provides a convenient grip for the patient or other person administering the gas.

The inlet section 5 comprises a hose connector 6 which is rotatably fitted in a hollow cylindrical bore of a valve seat member 7 which is itself mounted within the lower cylindrical portion of body 1. Sealing between the hose connector 6 and the seat member 7 is effected by an O-ring 8, while sealing between the seat member 7 and the lower cylindrical portion 3 of the body is effected by an O-ring 9. Socket head screws 10 retain the hose connector 6 and seat member 7 in the body 1. To this end, the heads of the screws are a close fit in holes in the body and are fitted in threaded holes in the seat member so as to hold the seat member securely in the body and prevent its rotation. The radially inward ends of the screws 10 fit into a radial groove extending 360° around the hose connector 6 to prevent the hose connector from moving axially, but enabling it to freely rotate.

The lower end of the hose connector 6 is formed with a serrated nozzle section over which fits the end of a gas supply hose 11. The hose connector is formed with a central bore 12 which communicates with the hose to carry gas from the gas supply into a chamber 13 below the valve seat itself.

Figure 4:
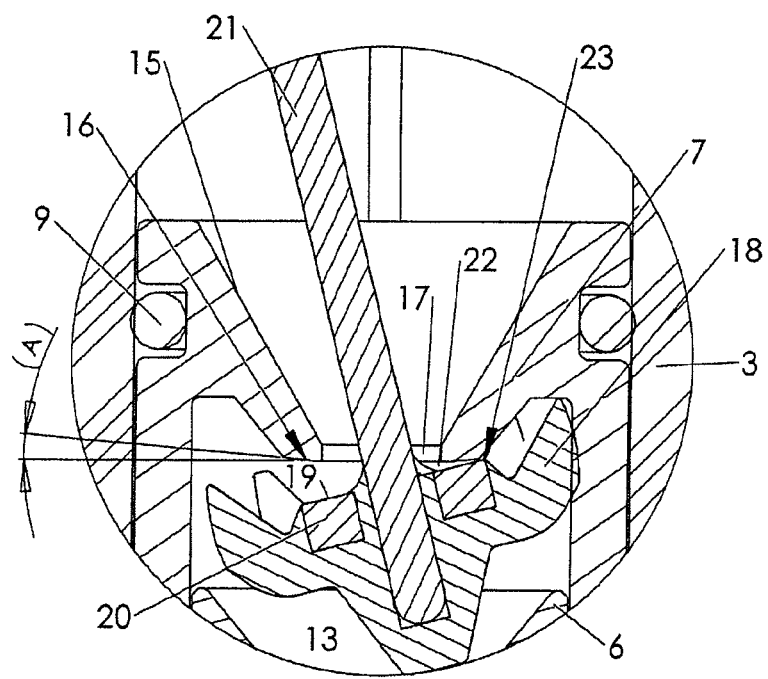
FIG. 4 is an enlarged view of part of FIG. 2, illustrating the regulator valve construction in greater detail.
Figure 5:
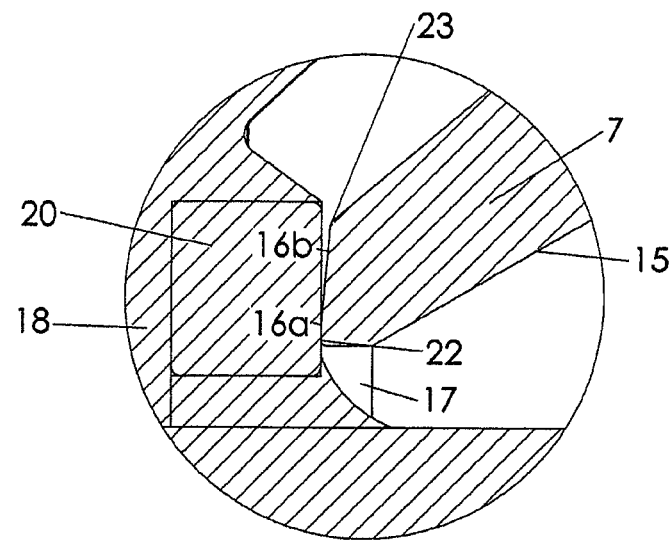
FIGS. 5 to 7 are still further enlarged views of part of FIG. 4, illustrating different arrangements for the valve seat.
Figure 6:
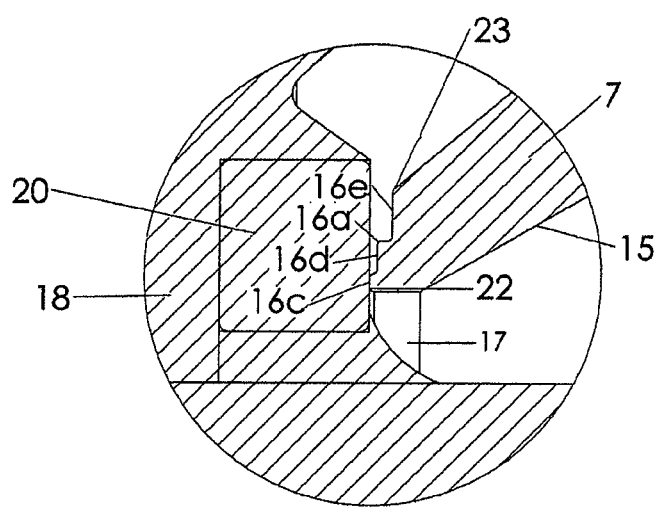
Figure 7:
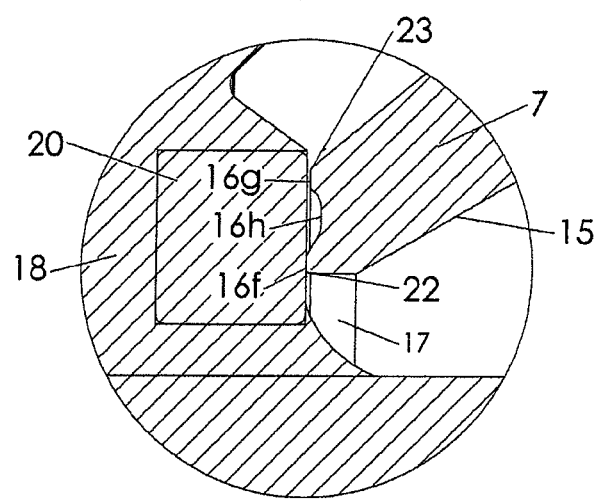

The valve seat is formed in the upper part of the seat member 7 and is shown in enlarged detail in FIG. 4 and still further enlarged detail in FIGS. 5 to 7. The upper surface 15 of the seat member 7 is generally frusto-conical in shape having an aperture 17 at its bottom end. The downwardly facing annular surface 16 which surrounds the aperture 17 forms the valve seat. The valve seat may have a planar or frusto-conical surface but alternative preferred configurations are illustrated in FIGS. 5 to 7.

In FIG. 5 the radially inward part 16a of surface 16 is planar whilst the radially outward part 16b of surface 16 is frusto-conical in shape, with an angle A defined as shown. The angle A is small, typically in the range 1° to 5°. In FIG. 6, the annular surface 16 is formed as a series of steps: 16c, 16d and 16e stepping downwardly in the radially outwards direction. In FIG. 7, the annular surface 16 is formed as a radially inward surface 16f and radially outward surface 16g separated by a recessed portion 16h. The two surfaces 16f and 16g are parallel, but not coplanar, the surface 16g being set back a small distance from the surface 16f. The purpose of these arrangements will be described below.

The open bottom of the cone-shaped upper surface 15 of the seat member forms a valve aperture 17 in communication with the aforesaid chamber 13. The valve aperture is closed by a valve member 18 which has a generally conical shape with an annular flat (planar) face 19 which faces the valve seat 16. In the closed position of the valve member, shown in FIG. 1, the face 19 abuts against the valve seat 15, and closes the valve aperture 17. Sealing between the face 19 and valve seat 15 may be enhanced by an insert 20, for example of a hard material such as gemstone or hardened and ground steel, or of resilient material.

The valve is maintained in a closed position by means of gas pressure applied via the hose 11. This pressure is transmitted to chamber 13 and acts to force the valve member 18 into close contact with the valve seat. This effect is enhanced by making the external diameter of the valve member 18 a close (clearance) fit within the inside diameter of the cylindrical bore in the valve seat member 7. The outer surfaces of the valve member 18 are spherical in profile so that this close fit is maintained even when the valve member tilts to open the valve, as will be explained below. A series of holes or cut-outs (not visible) are formed around the outside diameter of the valve member 18 to allow gas to pass from the chamber 13, past the tilted valve member, and through the valve aperture 17.

Figure 2:
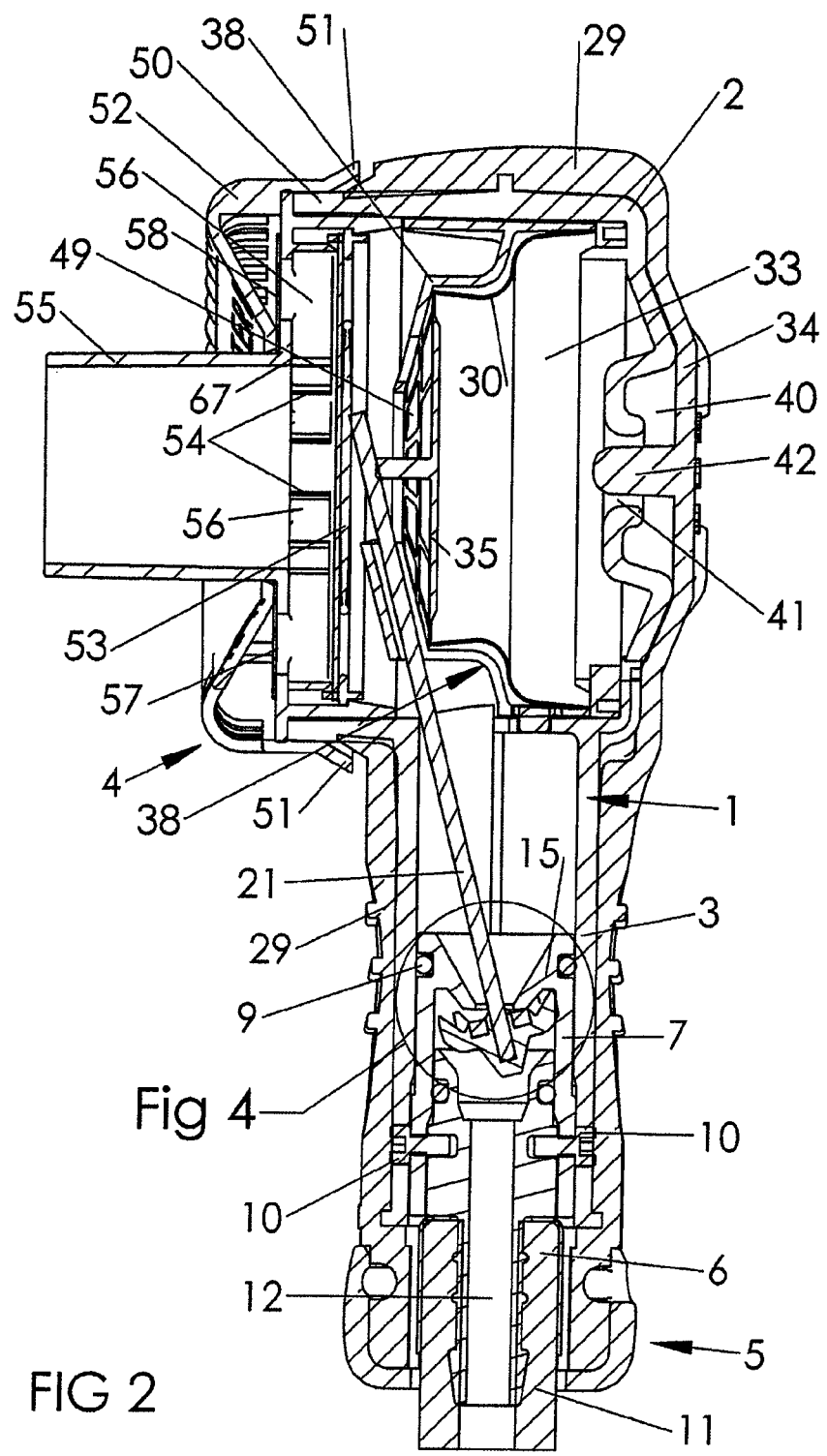

The valve is operated by force applied to a valve actuating rod 21 whose lower end is fitted to the valve member 18, and passes through the valve aperture 17, and whose upper end lies in the interior of the upper portion 2 of the body 1. As will be explained, a force applied to the upper end of the actuating rod 21 causes the valve member 18 to tilt, as shown in FIGS. 2 and 4, to allow gas to pass through the valve.

Referring to FIG. 4, it will be noted that, at the beginning of this tilting process, the pivot point of the valve member is the point 22, namely at the inner perimeter edge of the valve seat 16. As the valve member tilts beyond angle A, the pivot point transfers from point 22 to point 23 at the outer perimeter edge of the valve sat 15. With the transfer from point 22 to point 23, the mechanical advantage is reduced, thus increasing the force required to continue opening the valve. At the same time the difference in valve open area created by the same difference in angle of tilt also increases, as the sealing faces will move apart more for the same difference in tilt angle. This geometry allows for a lower cracking pressure—the pressure at which the valve just "cracks" open (see below)—for the same maximum flow, or a larger maximum flow for the same cracking pressure, or a smaller regulator for the same maximum flow, or a combination of all three.

The above explanation assumes that the whole width of the valve seat 16 is of conical shape. However, the same will apply if only the radially outer part of the valve seat is conical, with the radially inner part of the valve seat planar, as shown in FIG. 5. In another embodiment (not shown) both the radially inner and outer parts of the valve seat could be conical, but with a slightly greater angle A for the radially outer part. Such an arrangement will define three pivot points, spaced apart along the radial direction. The stepped arrangement of FIG. 6 will also be seen to define three pivot points spaced apart along the radial direction. In the case of FIG. 6, these pivot points are defined as the aforesaid points 22 and 23 with a further point 22a which is the nose of the step between surfaces 16d and 16e. In fact, it will be evident that more than three pivot points could be created, each at a larger diameter, to give a progressively higher opening force requirement as the member 18 tilts. These pivot points could be provided on the valve seat 16, the surface 19 or both. It would also be possible to profile the valve set 16 or surface 19, or both, to give a continuous variation in pivot length and thus a continuously reducing mechanical advantage as the sealing member tilts.

The arrangement of FIG. 7 will also be seen to provide a similar effect to that of FIG. 5 because the pivot point 23 is lower than the pivot point 22, due to the fact that the two surfaces 16g and 16f are not coplanar.

The upper end of the actuating rod 21 is operated by a diaphragm 30 situated in the upper portion 2 of the body 1. The external rim 31 of the diaphragm 30 is sealingly retained between the outer wall of the body 1 and a ring-like retaining wall 32 which extends from the upper portion 2 of the body 1, and integral therewith. In this way the diaphragm divides the interior of the upper portion 2 of the body 1 into two chambers, sealed from one another. To the right of the diaphragm, a chamber 33 is formed in the space between the diaphragm and the right-hand end wall 34 of the upper portion 2 of the body 1. The chamber 33 is vented to atmosphere by vent means (not shown). The vent means may comprise, for example, holes in the end wall 34, or advantageously may comprise passages (not shown) between the body 1 and cover 29, which vent to the exterior in the region around the gas inlet. This latter option would reduce ingress of water should the apparatus be dropped into water, for example during use in a birthing pool.

Figure 3:
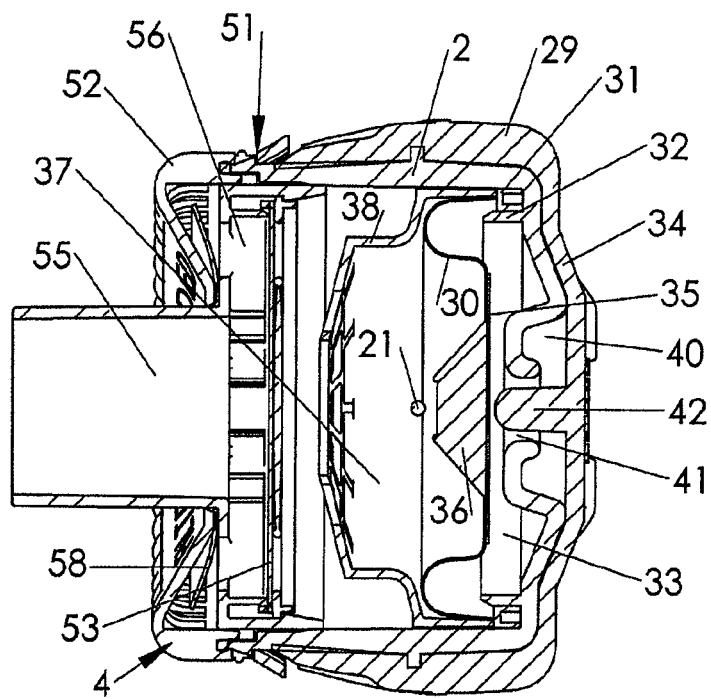
FIG. 3 is a sectional view on the lines A-A of FIG. 1.

The diaphragm 30 is made of flexible material, but is equipped with a semi-rigid disc 35 mounted centrally. Thus the disc 35 is free to move laterally from left to right and vice versa in FIG. 1. A small wall member 36 is mounted centrally of the disc 35, as shown in FIGS. 1 and 3. The height of the wall member is such that, in the relaxed stage of the diaphragm 30 shown in FIGS. 1 and 3, the wall member ends just short of the top end of the valve actuating rod 21. Thus, when the pressure in chamber 37, to the left of the diaphragm, is at atmospheric the diaphragm is in its relaxed state, and the valve remains closed.

A diaphragm retaining frame 38, made of rigid plastics material, is fitted into the upper portion 2 of body 1, for example by means of a snap fit. The frame 38 is of open construction, so as not to impede the gas flow, but is sufficiently extensive to ensure that the diaphragm 30 is securely retained. The frame 38 may also incorporate a cover grille to prevent users tampering with the diaphragm when the outlet unit 4 is removed. The frame preferably incorporates means 49 for deflecting gas flow entering the chamber 37 from hitting the diaphragm directly and possibly causing uneven breathing or vibration.

The right-hand wall 34 of the upper portion 2 of body 1 is formed with a shallow recess 40 at the bottom of which is an aperture 41 through which extends a protrusion 42, forming part of the flexible outer cover layer 29. The presence of the recess 40 allows the user to press the cover layer 29 into the recess, thus causing the protrusion 42 to engage the disc 35 forming the centre part of diaphragm 30, to thus cause the disc 35 to move a short distance to the left, and in turn cause the wall member 36 to engage the valve actuating rod 21 to crack open the valve. This feature can be used for test purposes to test for the presence of pressure (pressing the button should result in a hissing sound as gas escapes through the valve), or as a manual override to feed gas to the patient. The thickness and properties of the cover material over the recess 40 and the diameter of the recess 40 can be used to control the stiffness of operation.

The left-hand end of the upper portion 2 of body 1 defines an essentially circular rim 50 on which is removably mounted the outlet unit 4. As already explained, various means can be used for fixing the outlet unit 4 to the body 1, but the method shown comprises spaced clips 51 which engage a small shoulder formed on the exterior surface of rim 50.

The outlet unit 4, which is also shown in exploded view in FIG. 8, comprises a circular cover 52, incorporating apertures 59 for exhaled gas, and which fits on the rim 50 by means of the aforesaid clips 51. The cover 52 traps between itself and the edge of rim 50 a filter unit 60 carrying a circular disc filter element 53 held in place by an open frame 61.

The filter unit 60 comprises a hollow cylindrical section 65 which holds the filter element 53, and a connection tube 55. The connection tube is attached to the end wall 66 of the cylindrical section 65 and opens into the interior of the cylindrical section at an orifice 67. On the interior side of the end wall 66 are found a series of angularly spaced radially extending webs 54 which define between them a corresponding series of angularly-spaced chambers 56 for the passage of gas, as will be explained below. These webs 54 extend outwardly from the edge of the orifice 67 to the outer cylindrical wall of the cylindrical section 65. The filter element 53 is sandwiched between the frame 61 and the edges of the webs 54 to thus further define the extent of the chambers 56. The connection tube 55 may be one of the standard taper fittings used in this field, or any other connection means to which a means of connection to a patient's mouth may be sealingly fitted, such as a sample mouthpiece or mask (not shown).

The angularly-spaced chambers 56 define passageways through which gas may flow both in a generally axial direction of the filter unit (i.e. the horizontal direction in FIG. 1) towards the connection tube 55, and in a radial direction, and whether gas flows in one of these directions or the other, depends upon whether the patient is inhaling or exhaling, as will be explained. At their radially outer ends, the chambers 56 communicate with respective apertures 57 in the end wall 66, which apertures are closed by an annular flap valve element 58. The flap valve is seen to be open in FIG. 1, and closed in FIG. 2.

In use, the connection tube 55 is applied to the patient's mouth, for example via a mouthpiece (not shown). For this purpose the apparatus may be held by grasping the lower portion 3 of body 1. When the patient inhales, this causes a negative pressure in chamber 37 which causes the diaphragm 30 to move to the left, eventually reaching the position shown in FIG. 2. At the same time, the negative pressure causes the flap valve element 58 to remain closed. The tilting of the valve actuating rod 21 causes the valve member 18 to tilt and open the valve, thus supplying gas through the valve, into the chamber 37, and thence to the patient via the filter element 53 and connector 55. The gas entering chamber 37 acts to re-pressurise the chamber 37 so that a balanced condition is reached according to the demand of the patient.

In its normal state, shown in FIG. 1, the valve member 18 is pressed hard against the valve seat 16, due to the pressure originating in the gas source. The diaphragm 30 meanwhile, is in its relaxed state, with atmospheric pressure in both of chambers 33 and 37. When the pressure in the chamber 37 falls, due to patient inhalation, there comes a point at which the pressure in chamber 37 is sufficiently below atmospheric (the cracking pressure) that the pressure difference across the diaphragm 30 times the effective area of the diaphragm 30 times the effective length of the actuating rod 21 is greater than the supply pressure in chamber 13 times the effective area of the valve seat 16 times half the valve seat diameter at the edge contact point 22 between the valve seat and the valve member 18, to cause the valve member 18 to tilt away from the valve seat causing the valve to crack open.

With the valve open, the difference between the supply pressure and that in chamber 37 causes gas to flow through the valve. If the patient draws gas from the apparatus, as the drawn flow increases, so the diaphragm 30 will move further to the left causing the actuating rod 21 to tilt further in an attempt to maintain the pressure in chamber 37 substantially constant, thus allowing more flow through the valve to satisfy the demand. If the drawn flow decreases, the diaphragm 30 will move to the right, which allows the actuating rod 21 to tilt less to thereby balance the flow of gas through the valve in accordance with the lowered demand. When the pressure falls below the cracking pressure, the valve will close.

Thus, at the beginning of exhalation, the apparatus is once again in the state shown in FIG. 1, with the valve closed, and the diaphragm 30 in the relaxed state. In this state, the chamber 37 is effectively sealed against flow through the filter element 53 and into the chamber 37, since the flow has nowhere to go. Thus, when exhalation commences, the flow of exhaled gas back through the connector 55 encounters resistance in passing through the filter element 53 and into the chamber 37, and preferentially flows radially outwards, guided by the annular chamber 56, and exits to the exterior via the apertures 57 and flap valve element 58 which opens, as illustrated in FIG. 1, upon sensing the exhale pressure. Thus the exhaled gas does not enter the interior of the apparatus, thus greatly reducing the danger of cross-contamination between patients.

As a result of the above arrangement, the filter element 53 needs only to handle inhalation, and not exhalation as well. This in turn means that the filter medium can be of a lighter grade than if a two-way flow had to be passed. The resistance of the filter can thus be materially reduced, to a level in fact in which its presence is barely perceptible to the patient.

Advantageously, the outlet unit 4 is constructed as a single-use item, which is replaced with every patient. All parts of the regulator that come into contact with the patient's breath are disposed of, considerably reducing the possibility of transmission of infection from one patient to the next.

A manifold (not shown) may be fitted over the outlet unit 4 to duct the exhaled gas exiting through the exhale valve to a standard waste gas connection. In confined spaces, this prevents the build up of exhaled gas, which may contain a significant proportion of anaesthetic gas, in the ambient air.

It will be understood that the particular regulator described above is only one example of several types that could be used. For example, the regulators described in the aforementioned patents GB 2274595 (negative pressure) or GB 2190001 (positive pressure) could be used in conjunction with the replaceable outlet unit 4.

The medical breathing apparatus described above is constructed in such a way that its functions can be achieved with a minimum of parts. The body 1 can be constructed from a single moulding with one side-action: one opening for the gas supply and a second opening, to which the outlet unit can be directly connected. This requires no additional means of retention and can result in comparatively lower cost, both from the point of view of parts, and of assembly time compared to other constructions of regulator. There are no unnecessary sealing points, making the design inherently more reliable than known designs.

In addition, the construction allows very simple dismantling with only one Allen key required to completely disassemble the unit, so full decontamination is very simple to achieve.

The invention claimed is:

1. A medical breathing apparatus comprising a demand valve for regulating an input supply of breathing gas and passing the gas on demand to an outlet for application to a patient, said apparatus being characterized in that said outlet comprises a removable outlet unit comprising a contamination barrier and an exhale valve located on a downstream side of the contamination barrier with respect to the input supply of breathing gas.

2. The apparatus according to claim 1 in which the contamination barrier is a filter.

3. The apparatus according to claim 1 wherein the demand valve comprises pressure sensing means for sensing a negative inhale pressure of the patient and opening a regulator valve in response thereto to supply breathing gas from said input supply to the patient.

4. The apparatus according to claim 3 wherein said pressure sensing means comprises a hollow body containing a diaphragm which divides the hollow body into two chambers, one of which is a pressure sensing chamber.

5. The apparatus according to claim 4 in which the other of said two chambers is vented to atmosphere.

6. The apparatus according to claim 3 in which the pressure sensing means is arranged such that the demand valve remains closed unless the negative inhale pressure becomes greater than a predetermined level.

7. The apparatus as claimed in claim 1 wherein the outlet unit comprises a connector for connection to a mouthpiece or face mask to be worn by the patient, the inner end of the connector having flow means connecting the connector to the exterior via the exhale valve.

8. The apparatus as claimed in claim 7 wherein said flow means comprises a plurality of angularly spaced radially-extending webs defining angularly spaced chambers for directing exhaled gas from the connector to the exhale valve.

9. The apparatus as claimed in claim 8 wherein the exhale valve comprises a series of apertures formed at the outer end of said chambers, which apertures are covered by an annular flap valve element which normally closes the apertures, but which lifts to allow venting of the chambers when the pressure in the chambers rises as a result of exhalation.

10. The apparatus as claimed in claim 8 in which the contamination barrier is positioned against said radially-extending webs so as, during exhalation, to tend to direct the exhaled gas in a radial direction through the chambers but, during inhalation, to allow inhaled gas to pass from the demand valve, through the contamination barrier and into the connector.

11. The apparatus as claimed in claim 1 in which the demand valve is housed in a body, and said outlet unit comprises means for releasably fitting the outlet unit to the demand valve body.

12. The apparatus as claimed in claim 11 wherein said means for releasably fitting comprises a plurality of spaced clips which releasably latch onto the demand valve body.

13. The apparatus as claimed in claim 11 wherein said means for releasably fitting comprises a threaded or bayonet connection with said demand valve body.

14. The apparatus according to claim 1 wherein said demand valve comprises a valve comprising a valve seat and an associated valve member which is tiltable with respect to said valve seat to open and close the valve, and wherein there are provided two or more spaced pivot points between the valve member and valve seat, about which pivot points the valve member and valve seat progressively pivot as the valve moves from a closed position to an open position and vice versa.

15. The apparatus according to claim 1 in which the removable outlet unit is disposable.

16. A medical breathing apparatus comprising: a regulator for regulating an input supply of breathing gas and passing the gas on demand to an outlet for application to a patient, said apparatus being characterized in that said regulator comprises a valve comprising a valve seat and an associated valve member which is tiltable with respect to said valve seat to open and close the valve, and wherein there are provided two or more spaced pivot points between the valve member and valve seat, about which pivot points the valve member and valve seat progressively pivot as the valve moves from a closed position to an open position and vice versa.

17. The apparatus as claimed in claim 16 wherein said valve member has a valve surface which engages said valve seat to close the valve, and wherein said valve seat or said valve surface is at least in part of conical shape.

18. The apparatus as claimed in claim 17 wherein an angle A subtended between the side of the cone and a plane orthogonal to the axis of the cone is in the range of 1 degrees to 5 degrees.

19. The apparatus as claimed in claim 17 wherein said valve seat or said valve surface is formed of successive rings of conical shape, each of said rings having a slightly larger angle A from a previous ring, the angle A being defined as that subtended between the side of the cone and a plane orthogonal to the axis of the cone, so as to provide a reducing mechanical advantage in operation of the valve as the valve opens.

20. A medical breathing apparatus comprising a demand valve for regulating an input supply of breathing gas and passing the gas on demand to an outlet for application to a patient, said apparatus being characterized in that said outlet comprises a removable outlet unit comprising a contamination barrier and an exhale valve located on a downstream side of the contamination barrier with respect to the input supply of breathing gas, the unit being free of other valve types.

21. The apparatus according to claim 20 in which the contamination barrier is a filter.

* * * * *

UNITED STATES PATENT AND TRADEMARK OFFICE
CERTIFICATE OF CORRECTION

PATENT NO. : 8,448,643 B2 Page 1 of 1
APPLICATION NO. : 11/720816
DATED : May 28, 2013
INVENTOR(S) : Andrew Richard Thomas Tatarek It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1681 days.

Signed and Sealed this
Eighth Day of September, 2015

Michelle K. Lee
*Director of the United States Patent and Trademark Office*